(12) United States Patent
Axtell et al.

(10) Patent No.: US 7,211,707 B2
(45) Date of Patent: May 1, 2007

(54) MULTI-FUNCTIONAL PROTECTIVE MATERIALS AND METHODS FOR USE

(75) Inventors: Holly C. Axtell, Factoryville, PA (US); Scott M. Hartley, Clarks Summit, PA (US); Sallavanti Robert A., Dalton, PA (US)

(73) Assignee: Gentex Corporation, Carbondale, PA (US)

( * ) Notice: Subject to any disclaimer, the term of this patent is extended or adjusted under 35 U.S.C. 154(b) by 619 days.

(21) Appl. No.: 10/372,537

(22) Filed: Feb. 24, 2003

(65) Prior Publication Data

US 2003/0216256 A1    Nov. 20, 2003

Related U.S. Application Data

(60) Provisional application No. 60/360,050, filed on Feb. 25, 2002.

(51) Int. Cl.
*A62D 3/00* (2006.01)
*C01B 31/08* (2006.01)

(52) U.S. Cl. .................. 588/299; 210/749; 502/417

(58) Field of Classification Search ............... 502/417; 423/210; 210/749; 588/299
See application file for complete search history.

(56) References Cited

U.S. PATENT DOCUMENTS

| | | | |
|---|---|---|---|
| 3,746,655 A * | 7/1973 | Urbanic ............... 502/416 |
| 4,242,226 A | 12/1980 | Siren |
| 4,397,907 A | 8/1983 | Rosser et al. |
| 4,569,895 A | 2/1986 | Willett et al. |
| 4,610,905 A | 9/1986 | von Blucher et al. |
| 4,797,318 A | 1/1989 | Brooker et al. |
| 4,831,011 A * | 5/1989 | Oikawa et al. ........... 502/406 |
| 5,014,355 A | 5/1991 | Vollenweider, II |
| 5,032,209 A | 7/1991 | Shinbach et al. |
| 5,092,008 A | 3/1992 | Okubo |
| 5,482,773 A | 1/1996 | Bair |
| 5,486,410 A | 1/1996 | Groeger et al. |
| 5,582,913 A | 12/1996 | Simons |
| 5,620,643 A | 4/1997 | Maiden et al. |
| 5,639,307 A | 6/1997 | Bellemare |
| 5,690,705 A | 11/1997 | Holmes et al. |
| 5,712,219 A | 1/1998 | Klabunde et al. |
| 5,736,473 A | 4/1998 | Cohen et al. |
| 5,759,939 A | 6/1998 | Klabunde et al. |
| 5,914,436 A | 6/1999 | Klabunde et al. |
| 5,952,125 A | 9/1999 | Bi et al. |
| 5,962,082 A | 10/1999 | Hendrickson et al. |
| 5,965,479 A * | 10/1999 | Suzuki et al. ............ 502/182 |
| 5,972,808 A | 10/1999 | Groeger et al. |
| 5,989,514 A | 11/1999 | Bi et al. |
| 5,990,348 A | 11/1999 | Lyons et al. |
| 5,990,373 A | 11/1999 | Klabunde |
| 6,024,813 A | 2/2000 | Groeger et al. |
| 6,037,019 A | 3/2000 | Kooyer et al. |
| 6,043,184 A | 3/2000 | Karmakar et al. |
| 6,045,650 A | 4/2000 | Mitchnick et al. |
| 6,057,488 A | 5/2000 | Koper et al. |
| 6,060,419 A | 5/2000 | Wijesekera et al. |
| 6,074,437 A | 6/2000 | Racheria et al. |
| 6,087,294 A | 7/2000 | Klabunde et al. |
| 6,093,236 A | 7/2000 | Klabunde et al. |
| 6,113,807 A | 9/2000 | Yamaura et al. |
| 6,169,202 B1 | 1/2001 | Wijesekera et al. |
| 6,235,673 B1 | 5/2001 | Zoeller et al. |
| 6,294,222 B1 | 9/2001 | Cohen et al. |
| 6,316,378 B1 | 11/2001 | Giebelhausen et al. |
| 6,376,404 B1 | 4/2002 | Giebelhausen et al. |
| 6,387,531 B1 | 5/2002 | Bi et al. |
| 6,417,423 B1 | 7/2002 | Koper et al. |
| 6,607,994 B2 | 8/2003 | Soane et al. |
| 6,653,519 B2 | 11/2003 | Koper et al. |
| 6,761,761 B1 | 7/2004 | Schilling et al. |
| 6,827,766 B2 | 12/2004 | Carnes et al. |
| 6,843,919 B2 | 1/2005 | Klabunde et al. |
| 6,860,924 B2 | 3/2005 | Rajagopalan et al. |
| 6,887,302 B2 | 5/2005 | Rajagopalan et al. |
| 2002/0028333 A1 | 3/2002 | Giebelhausen et al. |
| 2002/0035032 A1 | 3/2002 | Koper et al. |
| 2002/0187258 A1 | 12/2002 | Bellemare et al. |
| 2003/0013369 A1 | 1/2003 | Soane et al. |
| 2003/0215355 A1 | 11/2003 | Lanz et al. |
| 2003/0220195 A1 | 11/2003 | Axtell et al. |
| 2004/0009726 A1 | 1/2004 | Axtell et al. |
| 2005/0026778 A1 | 2/2005 | Axtell et al. |

FOREIGN PATENT DOCUMENTS

JP    5131136    5/1993

* cited by examiner

*Primary Examiner*—Stuart Hendrickson
(74) *Attorney, Agent, or Firm*—Keusey, Tutunjian & Bitetto, P.C.

(57) ABSTRACT

A reactive-adsorptive protective material having an activated carbon adsorbent for adsorbing chemical impurities, wherein nanoparticular entities are loaded into and onto a surface of said activated carbon adsorbent to further impart chemically reactive and biocidal properties onto the activated carbon for providing protection against chemical and biological agents in the atmosphere. Advantageously, a superior reactive-adsorptive material is provided having the ability to kill microorganisms in addition to the ability to neutralize and decompose chemical substances, while at the same time not diminishing the adsorptive/reactive capabilities and effectiveness of either the substrate carbon or the loaded nanoparticular entities used.

13 Claims, 1 Drawing Sheet

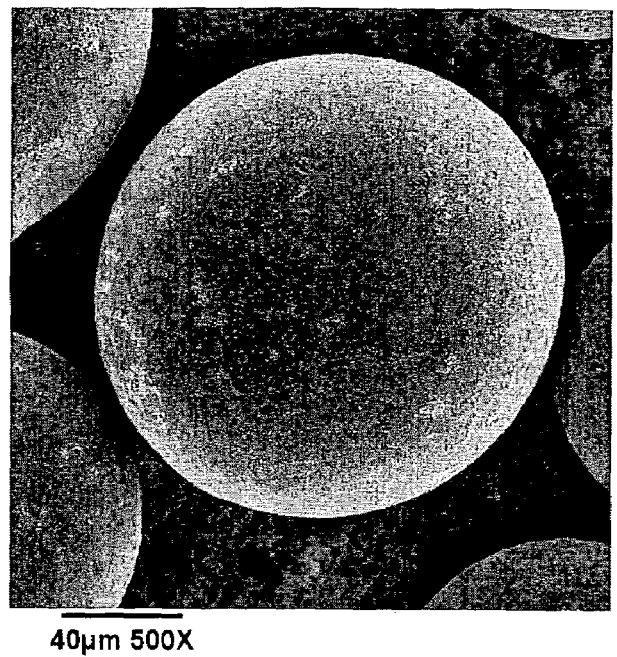
40μm 500X
FIG. 1-Untreated Ambersorb Carbon
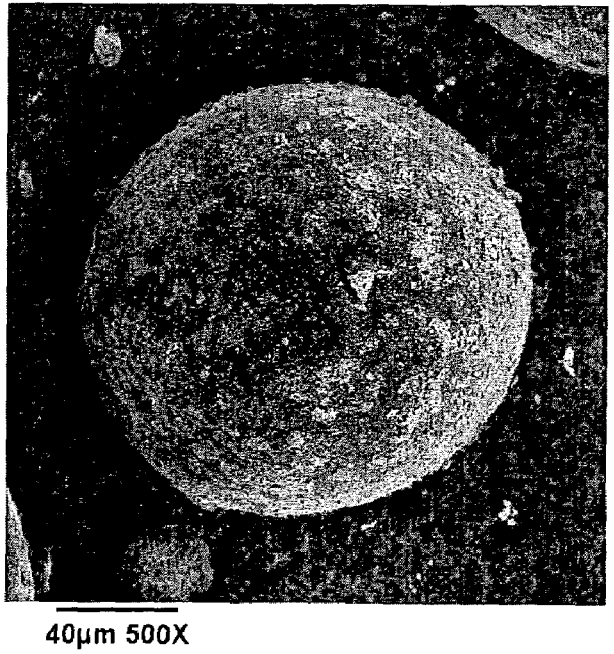
40μm 500X
Fig. 2 - Ambersorb Bead -- 1% treated MgO Nanoparticles

MULTI-FUNCTIONAL PROTECTIVE MATERIALS AND METHODS FOR USE

CROSS-REFERENCE TO RELATED APPLICATIONS

This utility application claims the priority date benefit of U.S. Provisional Application 60/360,050 filed on Feb. 25, 2002.

BACKGROUND OF THE INVENTION

1. Technical Field

The present invention relates generally to protective materials, and in particular, to reactive and adsorptive materials for providing multi-functional protection from chemical and biological agents and methods for providing and using such materials.

2. Description of Related Art

A) Chemical Agents

Agents of chemical warfare have existed for a long time and are generally grouped into the following three classes: 1) blister/percutaneous agents 2) nerve agents, and 3) blood agents.

1) Blister/percutaneous agents attack the skin and/or mucous membrane tissues external or internal to the human body, including the inhalation route. The resulting blistering and ulceration is extremely debilitating and can be fatal. Typical of this class is Mustard (labeled as Agent HD) which can be present as a liquid or a gas, or within an aerosolized carrier.

These agents were found early on to be readily absorbed by activated carbon which, when contained within canister beds or immobilized/fixed within or upon various textile substrates, offered the ready capability to absorb such agents and hold them away from vulnerable body areas of the person to be protected. Activated carbon has been made into and presented as powders, granules, dried slurries, fibers, spherical beads, etc. and is derived from a variety of processes which are performed on organic precursors such as coconut husks, wood, pitch and organic resins. Each process is unique but can be reduced in view to the following steps: (a) carbonizing the organic precursor material to carbon of modest internal surface area (of the order of tens to a few hundred of square meters or surface area per gram of carbon), and then (b) activating this carbon to produce a carbon with many hundreds to low thousands of $m^2/gm$ of surface area. Such activated carbon has strong adsorptive abilities. The word adsorb is important here. When a material adsorbs something, it means that it attaches to it by chemical attraction. The huge surface area of activated carbon gives it countless bonding sites. When certain chemicals pass next to the carbon surface they attach to the surface and are trapped.

The carbons worked with must be fixed within or upon a carrier substrate in order to be rendered into a useful form. Such fixation, whether by way of adhesion or entrapment or some other mode of fixing the carbon on the carrier, must be done deftly enough such that as little as possible of the valuable surface area is obfuscated by the fixation process.

2) The nerve agents comprise a variety of compounds which can be presented as gases, liquids or secured either in aerosol or other carriers, much as is HD. They attack the human body and interfere with nervous system functioning via immobilization of key enzymes necessary therein, causing death or severe injury. They all operate principally via percutaneous and inhalation routes and are extremely toxic even in miniscule amounts. Typical of such species are Sarin and Soman, often referred to as the G agents (GB and GD).

They are also efficiently absorbed by carbon of high surface area with the same carbon source/process and fixation considerations as discussed above.

3) The blood agents are those species which, when inhaled, dissolve via the lungs in the blood and cause asphyxiation by displacing the oxygen ($O_2$) normally carried by the hemoglobin moieties with more potently binding species known as strong Lewis Bases. Such agents include Hydrogen Cyanide (HCN), Carbon Monoxide (CO), Phosgene ($COCl_2$) and others. The blood agents are minimally and essentially ignorably absorbed by the activated carbon spoken of above. This is because the blood agents constitute molecules of too low a molecular weight such that their fugacity at normal temperatures exceeds any surface bonding power which the activated carbon can offer. Indeed, though activated carbon is good at trapping carbon-based impurities ("organic" chemicals), as well as things like chlorine, many other chemicals (sodium, nitrates, etc.) are not attracted to carbon at all, and therefore pass through unabsorbed. This means that an activated carbon filter will remove certain impurities while ignoring others.

It is to be noted that there are some chemical agents which can arguably be either percutaneous, inhalation or blood agents, or some combination of these simultaneously. However, for the purposes mentioned herein, such species would operationally fall into one or more of the modes of handling which are cited above.

B) Biological Agents

The agents of biological warfare include bacteria, viruses, fungi and spores (which some species generate as dormant "seeds" or genetic progenitors of themselves). The principal difference between biological agents and chemical agents is size; biological agents are larger, typically from one to a few tenths of a micron (1 micron=1 micrometer=$1\mu$=$1\times10^{-6}$ meter) up to multiples of microns for agglomerated colonies of same. Thus, biological agents are typically at least about a thousand times larger than chemical agent species.

All of the biological agents have membranaceous coatings for forming a self-containing protective sack around their vital components. These coatings may range from being lipids to lipoprotein and/or numerous variants thereof. These coatings are all stretched membranes, and the process of rupturing same is called lysis and defines the death of that entity as a biological agent. The contents within the membrane or the excreta of living biological entities can produce toxins which are not biological agents but instead are chemical agents whose molecular sizes are large but definitely within the molecular size category.

An effective mode of biological protection is to cover the person with an impenetrable barrier or "baggie" through which biological and even chemical entities cannot pass. However, human life's requirements of breathing, respiring and maintaining a not unacceptably high core body temperature under workload conditions make this solution unrealistic. Alternatively, the pores of activated carbon cannot absorb biological agents due to their size; they rapidly block the outer pores of carbon particles and deny them any further absorption ability. The use of biocidal materials which emit chemical entities upon/into biological intruders or through chemical and or mechanical contact cause lysis of the agent, is one possible mode of providing protection against biological agents. Such biocidal materials include a form of matter known as nanoparticular matter within which a huge portion of the atoms/ions thereof are at a surface of the particle. Such surface entities are very reactive toward organic chemical and biological entities and are also very small with jagged edges; both these features assist in causing the desired lysis of biological agents.

To fulfill a long standing need to provide biocidal components for protective systems for military and civilian EMS applications, scientists have been developing metal-based nanoparticles. U.S. Pat. No. 6,057,488 discloses effective biocidal properties of metal-oxide nanoparticles when dispersed as a powder or combined in a test tube with biological contaminants. Due to the unique physical properties and size of nanoparticles, it has heretofore been impossible to separate and fix the nanoparticles into a tangible form that could be flexibly integrated into protective systems and combined with conventional adsorbents.

Accordingly, a need exists for materials in a form which is easily handled during use and manufacturing of same which have improved adsorptive properties for more effective adsorption of impurities and which concurrently also have reactive and biocidal properties for adsorption and neutralization of chemical agents as well as destruction of biological agents.

SUMMARY OF THE INVENTION

The present invention is directed to reactive and adsorptive materials for providing protection from chemical and/or biological agents and methods for providing such materials. Advantageously, the present invention provides for efficient and effective adsorption and neutralization of harmful chemical agents as well as biological agents.

In one aspect of the present invention, a reactive-adsorptive protective material is provided comprising an activated carbon bead having adsorptive properties for adsorbing chemical impurities, and nanoparticular entities loaded onto said activated carbon bead to further impart chemically reactive and biocidal properties onto the activated carbon.

In yet another aspect, a method of producing a reactive-adsorptive multi-functional protective material is provided comprising the steps of providing activated carbon, the activated carbon having adsorptive properties for adsorbing chemical impurities, and loading nanoparticular entities into and onto a surface of said activated carbon to further impart chemically reactive and biocidal properties onto the activated carbon for providing protection against chemical and biological agents which are in contact therewith.

Advantageously, the present invention provides a process for converting powdered reactive, absorptive or protective materials into a manageable form while still maintaining an effective surface area of the powder. The present invention comprises a reactive-adsorptive protective particulate that combines the quick adsorptive kinetics of activated carbon with the destructive-adsorptive qualities of reactive nanoparticle technology, and thus provides not only chemical, but biological protection as well.

These and other aspects, features and advantages of the present invention will be described or become apparent from the following detailed description of the preferred embodiments, which is to be read in connection with the accompanying drawings.

BRIEF DESCRIPTION OF THE DRAWINGS

FIG. 1 depicts an exemplary SEM micrograph of an untreated carbon bead.

FIG. 2 depicts an exemplary SEM micrograph of a carbon bead loaded with 1% MgO particles according to an aspect of the present invention.

DETAILED DESCRIPTION OF PREFERRED EMBODIMENTS

As used herein, the term "activated carbon adsorbent" refers to any suitable form of activated carbon useful in protective applications. By way of non-limiting examples, the "activated carbon adsorbents" are beads, pellets, powders, granules, grains, tablets, particulates, fibers or dried slurries. A specific example having known utility is a bead having a highly uniform spherical shape. Such beads may be obtained from Rohm & Haas or Kureha. An activated carbonaceous bead (CarboTex bead) with an extraordinarily high surface area (e.g., about 1500 $m^2$/gm) and extraordinary hardness (e.g., from about 2 to about 10 times harder than Rohm & Haas and Kureha beads) is also used according to an aspect of the present invention. The materials and methods used for manufacturing the CarboTex activated carbon bead are described in published U.S. patent application Ser. No. 2002-0028333 entitled "Spherical High Performance Adsorbents with Microstructure" by Giebelhausen et al. filed on Mar. 8, 2001, U.S. Pat. No. 6,376,404 entitled "Process for the Production of Shaped High-Performance Adsorbents" by Giebelhausen et al. filed on Mar. 15, 2000, and U.S. Pat. No. 6,316,378 entitled "Process for the Production of Shaped Activated Carbon" by Giebelhausen et al. filed on Mar. 15, 2000, the disclosures of which are all incorporated herein by reference thereto.

It is to be noted that the materials preferably used for manufacturing the activated carbon used according to the present invention preferably comprise spherical high-performance adsorbents which are manufactured from polymer resin by water vapor activation with an activation time of at least 6 hours. These adsorbents have a pronounced microstructure in the range of about 0 Å to about 40 Å pore diameter and an overall micropore volume of at least 0.6 $cm^3$/g. A substantial increase in the adsorption capacity for gases and vapors is achieved which is also represented by the very favorable ratio of weight capacity to volume capacity of up to 2 to 1. The spherical high-performance adsorbents with microstructure can be used for many purposes, in particular, textile fabrics for the adsorption of chemical warfare agents and toxic gases and vapors, in adsorption refrigerating plants in combination with the refrigerating agent methanol, in motor vehicle filters and biofilters.

The spherical high-performance adsorbents, referred to as the CarboTex bead, preferably used in the present invention are explained in further detail by means of the following four exemplified embodiments.

EXAMPLE 1

Initially, 3 kg of a carbonized spherical cation exchanger polymer resin, sold under the designation Lewatit 1431, from Bayer AG, Leverkusen, having the following quality specification is selected as the starting material:

|  |  | Granulation: |  |
|---|---|---|---|
| Water content: | 1.1% | >1.25 mm | 0.2% |
| Volatile constituents: | 1.5% | 1.25 mm–1.0 mm | 5.1% |
| Ash content: | 2.4% | 1.0 mm–0.8 mm | 36.4% |
| Fixed carbon: | 96.1% | 0.8 mm–0.5 mm | 56.1% |
| Sulphur content: | 15.0% | <0.5 mm | 2.2% |

These gel-type resin beads are discontinuously activated for 7 hours in an inert gas flow in an indirectly heated tubular rotary kiln, with the product being circulated 8 times per kiln rotation, with the addition of 0.75 kg/hr water vapour at a low pressure on the flue gas side of 0.1 mm water column and with a product temperature of 920° C., with respect to the overall heated kiln length.

A total water vapor quality of 0.75 kg/hr is metered into the activation kiln as follows:

| | |
|---|---|
| 0.11 kg/hr | water vapour over 17% of the kiln length |
| 0.15 kg/hr | water vapour over 43% of the kiln length |
| 0.23 kg/hr | water vapour over 54% of the kiln length |
| 0.15 kg/hr | water vapour over 65% of the kiln length |
| 0.11 kg/hr | water vapour over 83% of the kiln length |

The kiln length is measured from the bead input side. Then the produced high performance adsorbents are cooled and screened as grain fractions between 0.315 mm and 0.8 mm in size.

The spherical high-performance adsorbents used in the present invention have a microstructure which is characterized by the following pore distribution:

| pore diameter (in Å Angstrom) | pore volume (in cm³/g) | pore volume content of overall micropore micropore volumes (in %) |
|---|---|---|
| 40–20 | 0.031 | 5.0 |
| 20–10 | 0.114 | 18.7 |
| 10–8 | 0.09 | 14.8 |
| 8–5 | 0.249 | 40.8 |
| 5–0 | 0.126 | 20.7 |

The measurable dust content, i.e., grains smaller than 0.04 mm is less than 1%. The remaining grain-size distribution is as follows:

| | |
|---|---|
| 0.7–0.63 mm | 0.2% |
| 0.63–0.5 mm | 12.3% |
| 0.5–0.4 mm | 78.2% |
| 0.4–0.315 mm | 9.3% |

The spherical high-performance adsorbents used in the present invention are characterized by the following quality parameters specific to activated carbon:

| | |
|---|---|
| Settled weight: | 585 g/l |
| Ash | 1.9% |
| Iodine value | 1388 mg/g |
| Methylene blue | 28 ml |
| BET surface | 1409 m2/g |
| Breaking strength | 100% |
| Dynamic hardness | 100% |
| Abrasion strength | 100% |
| Regeneration loss (after 10 regeneration cycles) | 1.5% |

Then, 500 g of the spherical high-performance adsorbents according to the invention are applied to a textile fabric, so that a high packing density is produced with a single-layer covering. The efficiency of the high-performance adsorbents used is measured in comparison with a test substance (reference substance for chemical warfare agents) characterized by the adsorption speed constant in accordance with the formula:

$\lambda = 2.3 \ldots \lg c_0/c_t \, a^{-1}$ a=weight of adsorbent sample
$c_t$=concentration of the test substance after the adsorption time
$c_0$=initial concentration of the test substance
lg=logarithm The measurement results in comparison with reference products are given in Table 1:

TABLE 1

| Product | Adsorption speed constant λ |
|---|---|
| PAX 500[1] | 3.2 |
| HK 44[2] | 2.3 |
| Ambersorb 572[3] | 2.1 |

[1] PAK 500: sample of spherical high-performance adsorbents with microstructure
[2] HK 44: activated carbon on charcoal base
[3] Ambersorb 572: pyrolised ion exchanger resin from Rohm & Haas, USA

EXAMPLE 2

The suitability of the spherical high-performance adsorbents for biofilter installations is tested in a laboratory bioreactor. For this the product as given in Example 1 is filled into the reactor chamber and immobilized with microorganisms up to a charging of $3.7 \times 10^9$ cells/g base material. Then 201/hr moist exhaust air with a toluene concentration of 500 mg/m³ are conveyed over the immobilized high-performance adsorbents. The achieved degradation capacity and the chamber charging with an efficiency of 90% are represented in Table 4.

TABLE 4

| Product | Degradation capacity (in g/m³ · h) | chamber charging at 90% efficiency (in g/m³ · h) |
|---|---|---|
| PAK 500[1] | 12.4 | 39.6 |
| WS IV[2] | 100.6 | 21.3 |
| C 40/3[3] | 74.5 | 14.5 |

[1] See Example 1
[2] WS IV: formed activated carbon (4 mm) on a charcoal base from Chemviron, Belgium
[3] C 40/3: formed activated carbon (3 mm) on a bituminous coal base according to the invention, CarboTex, Germany An activated carbon bead according to the present invention is preferably combined with reactive nanoparticles via an electromagnetically assisted impact collision (MAIC) process to form a multi-functional particulate. A reactive-adsorptive multi-functional protective particulate according to an aspect of the present invention advantageously possesses both chemically and biologically protective capabilities in a form which is easy to handle during use and manufacturing of same.

The reactive nanoparticles are supplied by Nanoscale Materials, Inc. of Manhattan, Kans. The nanoparticles advantageously have the capability of reacting with the toxic detritus/excreta of microorganisms while simultaneously not emanating oxidizing agents or any other agents which would pollute any nearby activated carbon. However, the nanoparticular particles are too small to be handled as such. It was found that for effective handling, the nanoparticles are preferably agglomerated into larger aggregates in a popcorn-ball style which preserves their surface to volume ratio of component atoms/ions and facilitates handling during manufacturing processes.

Due to the nature of the nanoparticulates, a multi-functional particulate according to the present invention also has the ability to provide, for example, effective biological protection without adversely affecting, for example, the reactive/adsorptive properties of the bead. Specifically, the multi-functional particulate comprises nanoparticular particles which have the capability of reacting with the toxic detritus/excreta of microorganisms while simultaneously not emanating oxidizing agents or any other agents which would pollute any nearby activated carbon within which the nanoparticles are imbedded.

The MAIC process imbeds the surface of activated carbon beads with the smaller reactive/adsorptive nanoparticles. Specifically, MAIC is a process which uses an electromagnetically induced impaction process in combination with simultaneous sieving so as to imbed nanoparticular agglomerated entities into the surface of carbon beads where they are held in place by the topographical imbedding in the carbon bead and the van der Waals forces between the particle ions and the carbon beads' surface/pore atoms proximate to the nanoparticle.

The MAIC process permanently imbeds the nanoparticulates into/onto the surface of the bead, thereby creating a unique multi-functional particulate. Thus, a reactive-adsorptive protective particulate is created that advantageously combines the quick adsorptive kinetics of activated carbon with the destructive-adsorptive-biocidal qualities of reactive nanoparticle technology. The resulting bead is therefore a hybrid, having at least two distinct, yet synergistic capabilities.

For example, the beads can be incorporated into, for example, permeable fabrics, reticulated foams, and filtration media. The textiles incorporating the reactive-adsorptive bead according to the present invention can provide protection from biological warfare agents or infectious microorganisms such as viruses, bacteria, sporulated bacteria, fungi or protozoa. The superior capabilities of the reactive-adsorptive bead can replace activated carbon in traditional textiles used by the military to protect soldiers from classic chermical warfare agents.

While the chemistries of the nanoparticles are intrinsically water soluble in some generated forms (e.g., MgO), other forms with protective coatings which are not soluble and thus do not lose reactivity have been created and can be used to create a multi-functional particulate according to the present invention. Additional forms of the nanoparticles may comprise e.g., nanoparticular CaO, $TiO_2$ and other inorganic species made by Nanoscale Materials, Inc.

In one example, Magnesium Oxide (MgO) nanoparticles in concentrations of 0.5, 1.0 and 2.0% by weight were loaded onto Ambersorb R-1500 carbon beads (produced by Rohm & Haas). For comparative purposes and for use as a control, Ambersorb carbon was processed in the MAIC system without the addition of nanoparticles. Visual observations of the treated samples indicated good attachment and distribution of the MgO on the Ambersorb carbon. FIG. 1 depicts an exemplary SEM micrograph of an untreated Ambersorb bead. FIG. 2 depicts an exemplary SEM micrograph of an Ambersorb bead loaded with 1% MgO nanoparticles according to an aspect of the present invention. This resultant treated particle illustrated in FIG. 2 has the appearance of a spherical "cookie" with "raisins" in its surface partially imbedded and partly exposed.

It is to be noted that the MAIC process can be used to load nanoparticles onto Kureha brand and Ambersorb brand carbon beads as well as the CarboTex activated carbon beads. In a preferred embodiment, when the MAIC treatment process is used to treat the Gentex activated carbon beads, the resulting bead advantageously boasts the combined qualities of the carbon's hyperadsorptivity as well as chemically reactive and biocidal properties due to the imparted nanoparticular entities, in an effective form which facilitates handling. Indeed, the nanoparticles would otherwise be difficult to handle by themselves. Such desirable qualities are advantageously achieved with one spherical entity of macroscopic dimension (e.g., about 0.4 mm in diameter) which is adjustable in size based on the dimensions of the precursor ion exchange resin beads used.

In a preferred embodiment for blood agent neutralization, along with biocidally reactive and chemically absorptive protection, carbon CarboTex beads are initially wettlerized and then processed to load nanoparticles thereon. When utilizing the preferred carbon beads, such treatment could combine the qualities of the carbon's hyperadsorptivity, metallic ions' avidity for blood agent chemistries, and chemically reactive and biocidal nanoparticular entities (which would ordinarily be difficult to physically handle alone but are now supported in the carbon bead carrier) into one spherical entity of macroscopic dimension (e.g., about 0.4 mm diameter, but tunable in size arbitrarily depending on the choice of dimension of the precursor ion exchange resin bead used). It is to be noted that the nanoparticles may be loaded into/onto any type, form or shape of activated carbon. An embodiment according to this aspect of the invention is disclosed in co-pending U.S. Patent Application entitled "Reactive-Adsorptive Protective Materials and Methods for Use" filed concurrently herewith, bearing U.S. patent application Ser. No. 10,372,352, and designated as—Carbon Beads and Metal Ions. The complete disclosure of this concurrently filed application is hereby incorporated by reference. In that embodiment activated carbon adsorbents are loaded with metal ions. Such a product may be further treated with protective nanoparticles according to the invention. As used in this application, the term "loaded" means a perfusion process or an infusion process or a wettlerization process to place metal ions on an activated carbon adsorbent.

Advantageously, the present invention overall provides a process for converting powdered reactive, absorptive or protective materials into a manageable form while still maintaining an effective surface area of the powder. The present invention comprises a reactive-adsorptive protective particulate that combines the quick adsorptive kinetics of activated carbon with the destructive-adsorptive qualities of reactive nanoparticle technology, and thus provides not only chemical, but biological protection as well. This multi-functional bead can be handled much as we classically handle carbon beads and be adhered to textiles, webs, fibers, etc. via classic use of selected adhesives, or via hot melt processes, etc. to generate laminates which present the chem/blood/bio properties into a roll goods form or web bed form. Indeed, it is envisioned that a multi-functional bead according to an aspect of the present invention can be incorporated into, but not limited to, permeable fabrics, reticulated foams, and filtration media.

It is to be noted that the activated carbon substrate used, regardless of its composition and origin, does not necessarily have to be spherical, but preferably has sufficient hardness and is of appropriate size to be utilized in the MAIC process. Indeed, a reactive-adsorptive multi-functional protective particulate according to the present invention may, for example, be spherical, non-spherical, a fragment or even a powder itself.

In addition, it is to be noted that the loading or concentration of nanoparticles on the surface of the carbon can be adjusted to increase or decrease particulate add-on. Once imbedded into the carbon, the reactive/adsorptive nanoparticulates are permanently bonded.

The nanoparticles preferably comprise environmentally stable nanometer-sized clusters of atoms and molecules having high surface areas and unique morphologies which result in high chemical reactivity. The reactive/adsorptive particulates used according to the present invention are preferably inorganic, reactive nanoparticulates formed from about 1 nm to about 200 nm sized clusters.

Reactive nanoparticles used for protective applications are specifically engineered to destructively adsorb chemicals and microorganisms. Specifically, a nanoparticle absorbs then detoxifies hazardous chemicals by breaking molecular bonds to yield harmless end products. Similarly, the reactive/adsorptive nanoparticles are able to kill or inactivate a microorganism by attacking its cell membrane and oxidizing important functional proteins or DNA.

Exemplary nanoparticles which may be used include metal oxide composites in powder nanoparticulate form. These metal oxide composites comprise metal oxide nanoparticles having oxygen ion moieties on their surfaces with reactive atoms interacted or chemisorbed with those surface oxygen ions. For example, the metal oxide nanoparticles may be taken from the group consisting of oxides of Mg, Ti, Ca, Al, Sn, Fe, Co, V, Mn, Ni, Cr, Cu, Zn, Zr, or mixtures thereof. For example, the metal oxide nanoparticles may comprise $MgO$, $TiO_2$, $CaO$, $Al_2O_3$, $SnO_2$, $Fe_2O_3$, $FeO$, $CoO$, $V_2O_5$, $MnO_3$, $NiO$, $Cr_2O_3$, $CuO$, $ZnO$, $ZrO_2$ and mixtures thereof. Nanoparticles made of metal complexes of hydroxides, metal complexes of hydrates as well as polyoxometallates (POMs) are also suitable. Some of the nanoparticles listed in this paragraph may also be further processed, for example to include reactive halogen atoms, alkali metal atoms, or a second different metal oxide. Alternate processing can provide a protective coating to the nanoparticles which are not soluble rendering them waterproof. These advanced processing steps are disclosed in the following U.S. Pat. Nos. 6,057,488 and 5,914,436 and 5,990,373 and 5,712,219 and 6,087,294 and 6,093,236 and 5,759,939 and 6,417,423 and in Published U.S. patent application Ser. No. 2002/0035032, the complete disclosures of which are incorporated herein by reference thereto. Any of these products may be incorporated into the multi-functional protective products according to the invention.

The reactive/adsorbent nanoparticulates are thus advantageously capable of:

a) Breaking down, decomposing or neutralizing chemicals (e.g. reactive/adsorptive nanoparticulates)

b) Acting as a biocide, killing microorganisms c) Neutralizing chemicals and simultaneously acting as a biocide (e.g. reactive/adsorptive-nanoparticulates such as MgO nanoparticles, etc.). These nanoparticles may be enhanced or modified for environmental purposes.

Thus, the nanoparticles preferably used according to the present invention include at least one of chemically adsorptive nanoparticles, chemically reactive nanoparticles, and biocidally reactive nanoparticles. Further, the nanoparticles used according to the present invention preferably have a Brunauer-Emmett-Teller (BET) multi-point surface area of at least about 70 $m^2/g$ for older nanoparticles to at least about 1200 $m^2/g$ or more for more advanced nanoparticles and have an average pore radius of at least about 45 Angstroms to at least about 100 Angstroms.

The MAIC treatment preferably used according to the present invention to imbed nanoparticles onto/into the carbon involves coating smaller particles onto larger particles by a peening process. By adding a smaller sized particle and a large core particle into an assembly of small oscillating magnets, the small particles are readily coated onto the larger core particles. The process is a continuous method in which the magnets are separated from the product and rates of 100–600 pounds per hour.

Advantageously, the MAIC process eliminates the need for adhesives and therefore minimizes the possibility of and concerns over occlusion or unwanted chemical reactions with the reactive/adsorbent nanoparticulates.

The MAIC process is further described by the following U.S. Pat. Nos. 5,032,209 and 6,045,650 and 6,037,019 and 5,620,643 and 5,962,082 and 4,569,895 and 5,690,705, the complete contents of which are incorporated herein by reference:

The nanoparticles used in accordance with the invention are those that possess a protective property, i.e. protective nanoparticles or protective nanoparticulate entities. For purposes of this application, the term "protective nanoparticles" encompasses one or more of the following three particular types of nanoparticles: chemically adsorptive nanoparticles; chemically reactive nanoparticles; and biocidally reactive nanoparticles.

Protective nanoparticles are metal-containing nanoparticles or metal-containing nanocrystals. The metals are present as metal oxides, metal hydroxides, metal hydrates, POMs. To enhance their protective properties, such metal-containing protectants may be combined with one of more of a metal oxide, Group I metals, Group IA metals, a reactive halogen, a metal nitrate, $SO_2$, $NO_2$, or ozone.

It should be noted that a bulk metal-containing particle that is ground down to a powder will not possess the protective properties of the nanoparticles used according to the invention because the ground powder will have conventional surface features. In order to distinguish powders from nanoparticles which may be seemingly in the same size range, the protectants according to the invention are referred to as finely divided nanoparticles or finely divided nanocrystals. Protective nanoparticles are formed from 1 nm to 200 nm sized nanoparticulate clusters. These clusters cling together due to van der Waals forces and therefore have many distinguishable constituent parts. A ground powder is just a single entity, with a uniform exterior surface. In contrast thereto, when the nanometer sized clusters cling together much of their original surface area is preserved providing Brunauer-Emmett-Teller (BET) multi-point surface areas of at least 70 $m^2/g$ for early protective nanoparticles and surface areas of at least 1200 $m^2/g$ for later versions. These surfaces may contain pores having an average pore radius from 45 Angstroms to 100 Angstroms.

While the structure, surface area and pore size have imbued the nanoparticles with their protective properties, these structural features have also interfered with past attempts to incorporate the nanoparticles into tangible protective filter precursors. Failed attempts have resulted from an inability to control the van der Waals forces resulting in excessive clumping or from an inability to control the adhesive or retaining means resulting in occluding of useful surface areas or pores. The invention is concerned with products and methods that utilize nanoparticles in a flexible manner to readily incorporate one or more of their chemically adsorptive, chemically reactive or biocidally reactive properties.

The nanoparticles used in accordance with the invention are those that possess a protective property, i.e. protective nanoparticles or protective nanoparticulate entities. For purposes of this application, the term "protective nanoparticles" encompasses one or more of the following three particular types of nanoparticles: chemically adsorptive nanoparticles; chemically reactive nanoparticles; and biocidally reactive nanoparticles.

Protective nanoparticles are metal-containing nanoparticles or metal-containing nanocrystals. The metals are present as metal oxides, metal hydroxides, metal hydrates, POMs. To enhance their protective properties, such metal-containing protectants may be combined with one of more of a metal oxide, Group I metals, Group IA metals, a reactive halogen, a metal nitrate, $SO_2$, $NO_2$, or ozone.

It should be noted that a bulk metal-containing particle that is ground down to a powder will not possess the protective properties of the nanoparticles used according to the invention because the ground powder will have conventional surface features. In order to distinguish powders from nanoparticles which may be seemingly in the same size range, the protectants according to the invention are referred to as finely divided nanoparticles or finely divided nanocrystals. Protective nanoparticles are formed from 1 nm to 200 nm sized nanoparticulate clusters. These clusters cling together due to van der Waals forces and therefore have many distinguishable constituent parts. A ground powder is just a single entity, with a uniform exterior surface. In contrast thereto, when the nanometer sized clusters cling together much of their original surface area is preserved providing Brunauer-Emmett-Teller (BET) multi-point surface areas of at least 70 $m^2/g$ for early protective nanoparticles and surface areas of at least 1200 $m^2/g$ for later versions. These surfaces may contain pores having an average pore radius from 45 Angstroms to 100 Angstroms. While the structure, surface area and pore size have imbued the nanoparticles with their protective properties, these structural features have also interfered with past attempts to incorporate the nanoparticles into tangible protective filter precursors. Failed attempts have resulted from an inability to control the van der Waals forces resulting in excessive clumping or from an inability to control the adhesive or retaining means resulting in occluding of useful surface areas or pores. The invention is concerned with products and methods that utilize nanoparticles in a flexible manner to readily incorporate one or more of their chemically adsorptive, chemically reactive or biocidally reactive properties.

Although illustrative embodiments of the present invention have been described herein, it is to be understood that the present invention is not limited to those precise embodiments, and that various other changes and modifications may be affected therein by one skilled in the art without departing from the scope or spirit of the present invention. For example, it is expressly intended that all combinations of those carbon beads, metal ions, nanoparticles and/or method steps and/or substrate materials which perform substantially the same function in substantially the same way to achieve the same results are within the scope of the invention. Moreover, it should be recognized that any disclosed form or embodiment of the invention may be incorporated in any other disclosed or described or suggested form or as a general matter of compatibility of application method. It is the intention, therefore, to be limited only as indicated by the scope of the claims appended hereto.

What is claimed is:

1. A method of combating a chemical or biological agent threat with an activated carbon-based decontaminant, comprising the steps of:
   loading protective nanoparticles onto an activated carbon adsorbent by electromagnetically induced impacting of said protective nanoparticles to imbed said protective nanoparticles into said activated carbon without interfering with the activated carbon adsorbent's ability to combat an adsorbable chemical threat; and
   exposing said adsorbent to an environment whereby the protective nanoparticles are adapted to combat the chemical or biological threat contained within the environment.

2. The method of claim 1, further comprising the step of sieving the protective nanoparticles during said impacting step.

3. The method of claim 1, wherein said protective nanoparticles comprise a material selected from the group consisting of chemically adsorptive nanoparticles, chemically reactive nanoparticles, biocidally reactive nanoparticles, and combinations thereof.

4. The method of claim 1, wherein said nanoparticles comprise a material selected from the group consisting of metal oxides, metal hydroxides, metal hydrates, POMs, and combinations thereof.

5. The method of claim 1, wherein said nanoparticles are combined with a material selected from the group consisting of a metal oxide, a reactive halogen, an alkali metal, a metal nitrate, $SO_2$, $NO_2$ ozone, and combinations thereof.

6. The method of claim 1, wherein said nanoparticles are formed from 1–200 nm sized nanoparticle clusters.

7. The method of claim 1, where said nanoparticles have a Brunauer-Emmett-Teller (BET) multi-point surface area of at least about 70 $m^2/g$ to at least about 120 $m^2/g$.

8. The method of claim 1, wherein said nanoparticles have an average pore radius of at least about 45 Angstroms to at least about 100 Angstroms.

9. The method of claim 1, further comprising the step of loading metal ions onto the activated carbon to further impart reactive properties onto the activated carbon for providing protection against blood agents which are in contact therewith.

10. The method of claim 9, wherein said step of loading metal ions occurs before said step of loading protective nanoparticles.

11. The method of claim 9, wherein said step of loading metal ions includes one of infusing metal ions, perfusing metal ions or wettlerizing metal ions.

12. The method of claim 9, wherein the metal ions comprise metallic salts.

13. A method of combating a chemical or biological agent threat with an activated carbon-based decontaminant, comprising the steps of:
   loading protective nanoparticles onto an activated carbon adsorbent by impacting of said protective nanoparticles to imbed the protective nanoparticles into the activated carbon without interfering with the activated carbon adsorbent's ability to combat an adsorbable chemical threat;
   sieving the protective nanoparticles during said impacting step; and
   exposing said adsorbent to an environment whereby the protective nanoparticles are adapted to combat the chemical or biological threat contained within the environment.

* * * * *